(12) United States Patent
Bowman et al.

(10) Patent No.: US 10,628,520 B2
(45) Date of Patent: Apr. 21, 2020

(54) CONFIGURABLE ANALYTICS FRAMEWORK FOR ASSISTANCE NEEDS DETECTION

(71) Applicant: International Business Machines Corporation, Armonk, NY (US)

(72) Inventors: Stephen D. Bowman, Monroe, NC (US); Kristin E. McNeil, Charlotte, NC (US); Philip E. Parker, York, SC (US)

(73) Assignee: International Business Machines Corporation, Armonk, NY (US)

( * ) Notice: Subject to any disclaimer, the term of this patent is extended or adjusted under 35 U.S.C. 154(b) by 49 days.

(21) Appl. No.: 15/591,645

(22) Filed: May 10, 2017

(65) Prior Publication Data

US 2018/0329875 A1    Nov. 15, 2018

(51) Int. Cl.
*G06F 3/00* (2006.01)
*G06F 17/24* (2006.01)
*G06F 17/27* (2006.01)
*G06Q 50/22* (2018.01)

(52) U.S. Cl.
CPC ........ *G06F 17/241* (2013.01); *G06F 17/2735* (2013.01); *G06Q 50/22* (2013.01)

(58) Field of Classification Search
CPC .... G06F 17/2735; G06F 17/278; G06Q 50/22
See application file for complete search history.

(56) References Cited

U.S. PATENT DOCUMENTS

| | | | |
|---|---|---|---|
| 9,372,924 B2 * | 6/2016 | Bostick | G06F 17/2785 |
| 9,378,200 B1 | 6/2016 | Cohen et al. | |
| 2005/0262039 A1 | 11/2005 | Kruelen et al. | |
| 2007/0041514 A1 * | 2/2007 | Rodkey | H04L 12/1895 379/37 |
| 2009/0248400 A1 | 10/2009 | Luke | |
| 2012/0199836 A1 | 8/2012 | Katsuhara et al. | |
| 2013/0024207 A1 * | 1/2013 | Anderson | G16H 10/60 705/3 |
| 2013/0167025 A1 | 6/2013 | Patri et al. | |
| 2015/0269642 A1 | 9/2015 | Cai et al. | |
| 2016/0124928 A1 * | 5/2016 | Fink | G06F 17/241 715/231 |
| 2016/0292371 A1 * | 10/2016 | Alhimiri | G06F 19/328 |

* cited by examiner

*Primary Examiner* — Kyle R Stork (74) *Attorney, Agent, or Firm* — Joseph Polimeni; SVL IP Law (57) ABSTRACT

According to an embodiment of the present invention, a system dynamically processes a document including unstructured text and comprises a computer system including at least one processor. Initially, the system configures a plurality of dictionaries with terms supplied by a user and associated with a desired category. The processor in the system applies a set of rules to the unstructured text of the document to detect patterns indicating a presence of the desired category, wherein the set of rules is re-usable across dictionaries configured for different categories and pertains to arrangements of dictionary terms within sentences. The system produces annotations associated with the desired category for the document based on the detected patterns. Embodiments of the present invention further include a method and computer program product for dynamically processing a document including unstructured text in substantially the same manner as is described above.

15 Claims, 9 Drawing Sheets

NEEDS ASSISTANCE WALKING PRIMARY ACTION DICTIONARY

| PRIMARYACTION | PART OF SPEECH |
|---|---|
| PRIMARYACTION 1 - 17. AMB - WALK | |
| abc AMB | VERB |
| abc AMBULATE | VERB |
| abc AMBULATION | VERB |
| abc AMBULATORY | VERB |
| abc GO FOR A JOG | VERB |
| abc GO FOR A RUN | VERB |
| abc GO FOR A WALK | VERB |
| abc JOG | VERB |
| abc MOBILITY | VERB |
| abc PACE | VERB |
| abc RUN | VERB |
| abc STEP | VERB |
| abc STROLL | VERB |
| abc TAKE A STEP | VERB |
| abc TAKE A STROLL | VERB |
| abc TAKE A WALK | VERB |
| abc WALK | VERB |

CONFIGURABLE ANALYTICS FRAMEWORK FOR ASSISTANCE NEEDS DETECTION

BACKGROUND

1. Technical Field

Present invention embodiments relate to natural language processing (NLP) systems, and more specifically, to a configurable analytics framework that facilitates assistance needs detection.

2. Discussion of the Related Art

With the significant growth of Web-based content, there is an increasing demand for text analytics to determine a need for patient and/or client assistance with various activities. For example, to ensure proper treatment strategies, a medical service provider may need to determine, in real-time, whether a patient needs help doing day-to-day activities such as walking, bathing, and/or going to the bathroom. Other concept areas in which text analytics may help service providers to determine client needs for assistance may include educational instruction, financial planning, legal, etc. Unfortunately, each target concept area associated with client and/or patient needs assistance may have different terms and/or modifiers associated with it. Accordingly, generating text analytics annotators to cover all of the variations of the target concept areas for assistance needs identification may be cost-prohibitive, if possible at all. For example, significant development effort would be required to create an annotator capable of identifying needs assistance terms and/or modifiers for each target concept area.

SUMMARY

According to an embodiment of the present invention, a system dynamically processes a document including unstructured text and comprises a computer system including at least one processor. Initially, the system configures a plurality of dictionaries with terms supplied by a user and associated with a desired category. The processor in the system applies a set of rules to the unstructured text of the document to detect patterns indicating a presence of the desired category, wherein the set of rules is re-usable across dictionaries configured for different categories and pertains to arrangements of dictionary terms within sentences. The system generates annotations associated with the desired category for the document based on the detected patterns. Embodiments of the present invention further include a method and computer program product for dynamically processing a document including unstructured text in substantially the same manner as is described above.

DETAILED DESCRIPTION

Present invention embodiments dynamically process a document including unstructured text, according to one or more configurable dictionaries, to identify whether an individual needs assistance performing one or more activities. A document comprising text and other information is retrieved and analyzed in accordance with one or more terms provided in the one or more configurable dictionaries. For example, a user may configure the one or more configurable dictionaries to process one or more documents related to a medical patient to determine whether the patient needs assistance with one or more daily activities (e.g., standing, walking, eating, dressing, bathing, using the toilet, speaking, administering a health substance, etc.). The text within the one or more documents are dynamically analyzed in real-time by one or more analysis techniques using a top-down heuristic searching algorithm to extract individual words or text from the document. The extracted information may be analyzed by one or more natural language processing ("NLP") techniques that match the extracted information with a corresponding term within the one or more configurable dictionaries to identify whether a person associated with the one or more documents needs assistance performing the one or more activities.

Accordingly, the disclosed system comprises a configurable framework that uses lexical analytic/parsing rules to detect language patterns that indicate whether one or more persons needs assistance to perform one or more activities associated with one or more preconfigured concept areas. The disclosed framework may be preconfigured to detect a need for assistance with one or more activities related to one or more concept areas (e.g., eating, walking, balancing checkbook, doing taxes, etc.). The disclosed framework may further search one or more documents for language patterns indicating that one or more assistive devices (e.g., cane, wheelchair, calculator, etc.) are required and/or used to perform the one or more activities related to the one or more concept areas.

The system may further comprise one or more configurable dictionaries that define features associated with a plurality of terms that may be used to identify whether one or more persons associated with the one or more documents needs assistance performing one or more activities. In so doing, the dictionaries effectively create one or more annotators based on the features identified in the one or more configurable dictionaries that may be used to detect needs assistance for various activities.

Accordingly, present invention embodiments utilize text analytics to perform text analysis on one or more documents in order identify whether an individual needs assistance performing one or more activities associated with a given concept area. The translated information resulting from the text analytics may be readily understood by a user, computerized process, and/or service professional (e.g., doctor, lawyer, financial advisor, etc.) to determine, in real-time, whether a person (e.g., user, client, patient, etc.) needs assistance with one or more activities (e.g., eating, walking, legal document preparation, tax preparation, etc.) and the type of assistance that should be provided.

Figure 1:
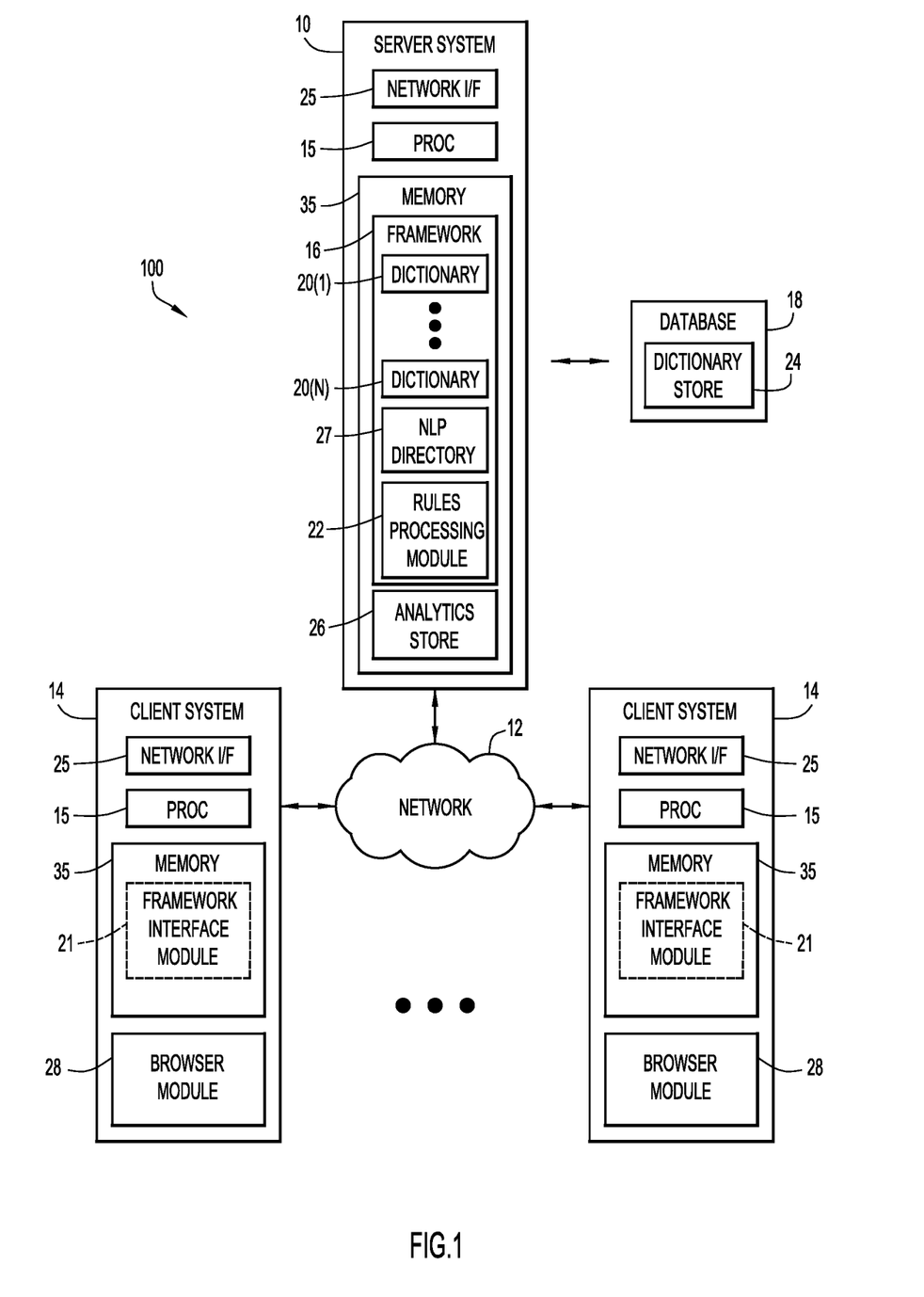
FIG. 1 is a diagrammatic illustration of an example computing environment for use with an embodiment of the present invention.

An example computing environment for use with present invention embodiments is illustrated in FIG. 1. Specifically, environment 100 includes one or more server systems 10, and one or more client or end-user systems 14. Server systems 10 and client systems 14 may be remote from each other and communicate over a network 12. The network may be implemented by any number of any suitable communications media (e.g., wide area network (WAN), local area network (LAN), Internet, Intranet, etc.). Alternatively, server systems 10 and client systems 14 may be local to each other, and communicate via any appropriate local communication medium (e.g., local area network (LAN), hardwire, wireless link, Intranet, etc.).

Client systems 14 enable users to retrieve documents (e.g., webpages, data files, etc.) from server systems 10, allowing the users to consume information corresponding to the retrieved documents. The server systems may include one or more configurable frameworks 16, which may comprise one or more configurable dictionaries 20, a rules processing module 22, one or more NLP dictionaries 27 and an analytics store 26 (e.g., a content analytics store (CAS)). Framework 16 generates annotations for terms retrieved from the original text of a document in view of corresponding terms and/or symbols stored in one or more dictionaries 20 and/or dictionary store 24. The one or more dictionaries 20 enable natural language processing (NLP) of a document text to identify words and/or terms associated with needs assistance detection as described below. Rules processing module 22 identifies patterns of text and/or phrases within the document text to apply corresponding rules for assistance needs detection. Analytics store 26 stores corresponding annotations to produce a resulting document for display to the requesting system and/or user device.

Accordingly, one or more dictionaries 20 may contain a plurality of terms and/or phrases related to assistance needs in one or more activities associated with one or more concept areas. For example, one or more dictionaries 20 may comprise a primary action dictionary that includes a plurality of terms and/or symbols associated with one or more primary functions (e.g., bathing, showering, eating, chewing, etc.) related to one or more activities (e.g., bathing, eating, etc.). One or more dictionaries 20 may further comprise a secondary action dictionary that includes a plurality of terms associated with one or more activities for which confirmation may be necessary to determine whether the one or more activities are related to the given concept area.

Similarly, one or more dictionaries 20 may also comprise an action implement dictionary that may indicate one or more implements associated with a secondary activity to a specific concept area such that the presence of the one or more implements in a phrase may indicate the specific concept area. For example, "holding" may be a secondary activity with respect to eating assistance. The action implement dictionary associated with eating assistance therefore may include one or more implements (e.g., utensils, tools, etc.) related to eating (e.g., fork, spoon, knife, etc.) such that the system may parse a phrase including the one or more implements (e.g., "difficulty holding a fork") to generate an eating assistance required annotation. Conversely, the system would not generate an eating assistance required annotation for the phrase "difficulty holding the door" because "holding" and "door" in this case are not related to eating assistance.

One or more dictionaries 20 may further comprise an assistive device dictionary that includes a plurality of terms indicating one or more devices used to perform a specific activity. For example, an assistive device dictionary may be preconfigured to be associated with walking assistance and therefore may include one or terms and/or symbols indicating one or more devices related to walking assistance (e.g., walker, cane, etc.).

A database system 18 may store various information for contextual analysis (e.g., user profiles, assistance information, etc.). Dictionary store 24 may reside in database system 18 or in memory 35 of server systems 10 and/or client systems 14 and contain dictionaries 20 and/or 27. The database system may be implemented by any conventional or other database or storage unit, may be local to or remote from server systems 10 and client systems 14, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information and/or documents for and/or from server systems 10.

Server systems 10 and client systems 14 may be implemented by any conventional or other computer systems preferably equipped with a display or monitor, a base (e.g., including at least one processor 15, one or more memories 35 and/or internal or external network interfaces or communications devices 25 (e.g., modem, network cards, etc.)), optional input devices (e.g., a keyboard, mouse or other input device), and any commercially available and custom software (e.g., server/communications software, rules processing module, browser/interface software, etc.).

The client systems may further include framework interface module 21 to provide a user interface to framework 16 on server systems 10, enabling a user to preconfigure one or more dictionaries 20 to include a plurality of terms and/or symbols associated with one or more activities related to a specific concept area such that framework 16 may annotate one or more documents in view of the terms and/or symbols associated with the one or more activities. Client systems 14 may further include a browser module 28 that may display a graphical user interface (e.g., GUI, etc.) or other interface (e.g., command line prompts, menu screens, etc.) to solicit information from a corresponding user to configure framework 16 on server systems 10. Alternatively, one or more client systems 14 may analyze documents and dynamically identify extracted information associated with required assistance needs (e.g., medical diagnosis, financial records, etc.) in a stand-alone mode of operation. In this case, client systems 14 may include framework 16, dictionary store 24, and analytics store 26 as described below.

Framework 16, framework interface module 21, rules processing module 22, and browser module 28 may include one or more modules or units to perform the various functions of present invention embodiments described below. The various modules (e.g., framework, framework interface module, rules processing module, browser module, etc.) may be implemented by any combination of any quantity of software and/or hardware modules or units, and may reside within memory 35 of server 10 and/or client systems 14 for execution by processor 15.

Figure 2:
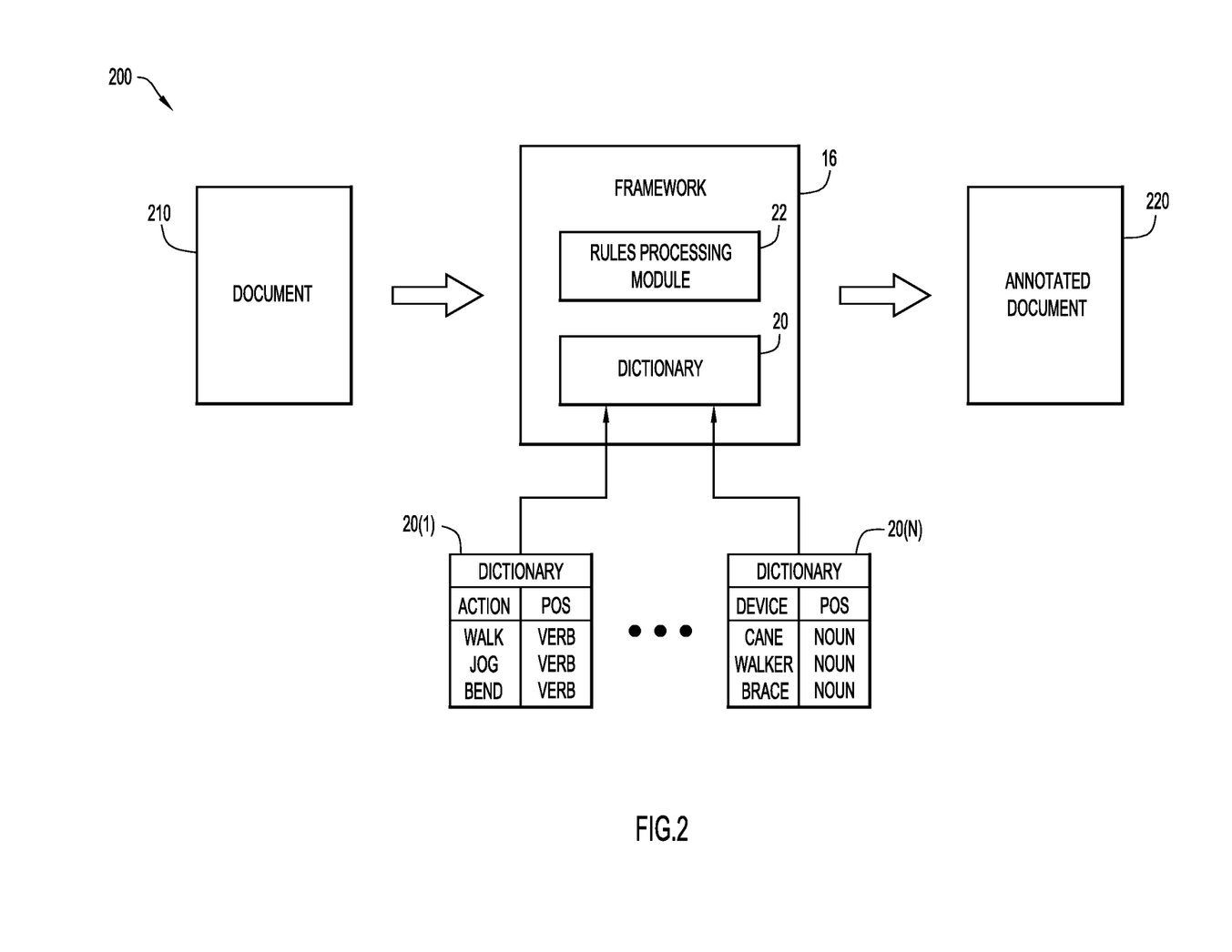
FIG. 2 is a diagrammatic illustration of an example process employing a configurable framework to produce an annotated document according to an embodiment of the present invention.

A process 200 in which a document is dynamically annotated with identified needs assistance terms is illustrated in FIG. 2. As shown in FIG. 2, one or more dictionaries 20 may be preconfigured to include a plurality of terms, phrases and/or symbols associated with one or more activities related to a specific concept area. For example, as further shown in FIG. 2, one or more dictionaries 20 may be preconfigured to indicate a plurality of action and/or device terms (e.g., walk, jog, bend, cane, walker, brace, etc.) and corresponding parts of speech (POS) (e.g., verb, noun, adjective, etc.) for needs assistance.

Initially, framework 16 in server systems 10 may receive and/or retrieve document 210, which may contain needs assistance information associated with one or more individuals who may need assistance performing one or more activities related to a specific concept area (e.g., walking, eating, standing, etc.). Framework 16 may be further configured to search for specific information (e.g., text, phrases, colloquialisms, and/or symbols) within document 210 and use an analyzer service (e.g., Watson Explorer Content Analytics Studio, Watson sentiment analyzer, etc.) to perform content analytics on the text in document 210. For example, framework 16 may use Watson Explorer Content Analytics Studio to create content analytics associated with document 210 that are suitable for use in Unstructured Information Management Architecture (UIMA) pipelines.

Using rules processing module 22, framework 16 may generate annotations associated with specific text within document 210 in view of the plurality of terms and/or symbols stored in one or more dictionaries 20. Thus, the annotators and annotations generated by framework 16 may utilize information within one or more dictionaries 20 to identify needs assistance terms and/or phrases associated with specific text within document 210. Framework 16 may generate annotated document 220 by modifying the original text in document 210 to include one or more annotations for the text identifying needs assistance terms and/or phrases.

According to an embodiment of the present invention, framework 16 may incorporate a natural language processing (NLP) system (e.g., APACHE UIMA) to perform context analytics on document 210. Accordingly, the individual text retrieved from document 210 may be unstructured, and entered into an Unstructured Information Management Architecture (UIMA) pipeline for processing (including annotation generation). The pipeline, by way of example, may be implemented by a native processing layer (e.g., JAVASCRIPT, etc.) on top of a JAVA or C++ implementation of UIMA from APACHE. The processing layer may be compliant with the NETSCAPE Plugin Application Programming Interface (NPAPI) which is a cross-browser Application Programming Interface (API) for plugin modules. Annotations that are produced by the UIMA pipeline may be displayed in the document in addition to the original text associated with the annotation. Framework 16 therefore may generate annotated document 220 by modifying the original text in document 210 to include annotations for the text associated with the corresponding annotations generated by the UIMA pipeline.

Figure 3:
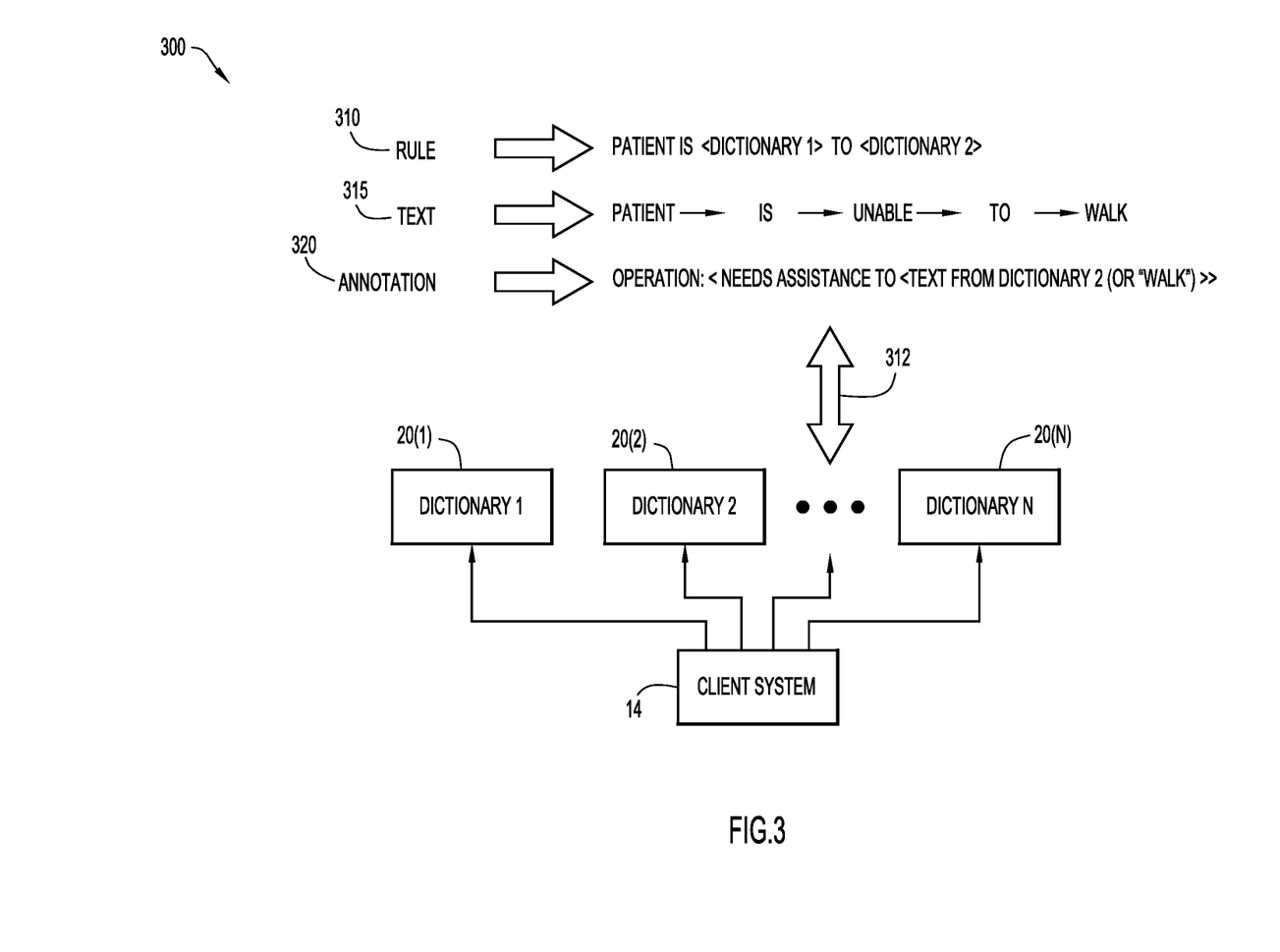
FIG. 3 is a diagrammatic illustration of an example manner in which an annotation for needs assistance is generated according to an embodiment of the present invention.

A process 300 in which a document is dynamically annotated for needs assistance is illustrated in FIG. 3. As shown in FIG. 3, one or more dictionaries 20 may be preconfigured by a user associated with client systems 14 to include a plurality of terms and/or symbols associated with one or more activities related to a specific concept area. For example, as further shown in FIG. 3, one or more dictionaries 20 may be preconfigured to allow framework 16 to determine whether an individual needs assistance performing a specific task or tasks (e.g., walking).

Initially, framework 16 in server systems 10 may receive a document related to an individual who may need assistance performing one or more specific tasks and may process the document via an analyzer (e.g., Watson Explorer Content Analytics Studio, Watson sentiment analyzer, etc.) to perform content analytics and/or to parse the document into specific text (e.g., text, phrases, colloquialisms, and/or symbols). Framework 16 may further generate annotations associated with a plurality of text and/or phrases in the document in view of the plurality of terms and/or symbols stored in one or more dictionaries 20. As such, the annotators and annotations generated by framework 16 may utilize information within one or more dictionaries 20 to identify needs assistance terms and/or phrases associated with the specific text (e.g., text, phrases, colloquialisms, and/or symbols) identified in the document.

Accordingly, using rules processing module 22, a rule 310 is applied to text 315 of the document. According to an embodiment of the present invention, a rule may specify a pattern with a term and/or phrase (e.g., "Patient is") including one or more references 312 to specific dictionaries 20 (e.g., <Dictionary 1>). The pattern is applied to text 315, where dictionary referenced in the rule are searched for the corresponding terms of the text. If the terms are present in the specified dictionaries, the text satisfies the rule and a corresponding annotation is produced. For example, as shown in FIG. 3, the terms "unable" and "walk" may reside in referenced dictionaries 20, thereby satisfying application of rule 310 to a given pattern in text 315 and enabling framework 16 to generate annotation 320.

Framework 16 may apply rule 310 to modify text 315 within a document to include annotation 320 to indicate whether an individual needs assistance performing one or more tasks. According to an embodiment, rules may be reused, whereby dictionaries 20 may be configured to enable application of the same rules for various different activities. For example, as shown in FIG. 3, framework 16 may use one or more terms stored in one or more dictionaries 20 to generate an annotation (e.g., "needs assistance to walk") associated with the phrase "patient is unable to walk." Thus, as further shown in FIG. 3, a user associated with client systems 14 may preconfigure one or more dictionaries 20 to include a plurality of needs assistance terms and/or phrases associated with one or more specific tasks to enable framework 16 to annotate a document to indicate whether and/or how an individual needs assistance performing one or more specific tasks.

Figure 4:
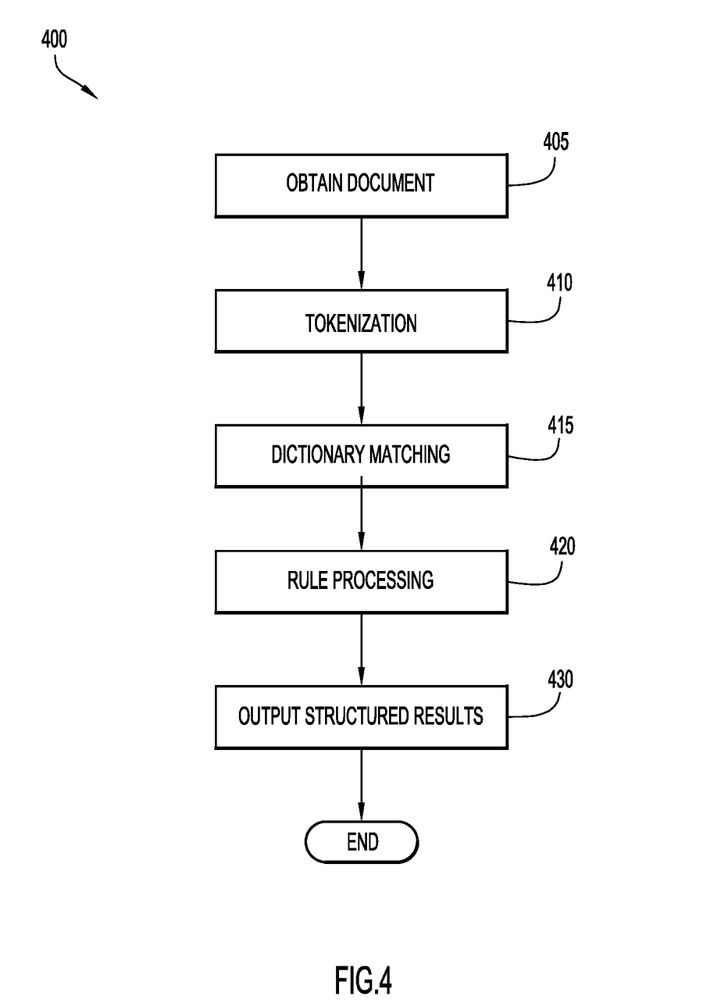
FIG. 4 is a procedural flow chart illustrating a process to dynamically produce an annotated document for needs assistance according to an embodiment of the present invention.

A process 400 in which individual terms, phrases and/or symbols within one or more documents are processed (e.g., via server systems 10 and/or client systems 14) to identify needs assistance indicators according to an embodiment of the present invention is illustrated in FIG. 4. Initially, one or more documents with needs assistance terms and/or phrases are retrieved at step 405. The one or more retrieved documents are preferably stored within memory 35 of server systems 10 and/or client systems 14, and/or within database system 18. Each of the one or more retrieved documents is associated with (or has documents produced by) one or more users who may need assistance performing one or more activities related to a specific topic. For example, a retrieved document may have contain information indicating that a patient needs assistance walking. The particular document to be retrieved may be specified by a user via framework interface module 21, and may include terms utilized by a group of service professionals (e.g., physicians, lawyers, financial experts, etc.).

Framework 16 may use an analyzer (e.g., Watson context analyzer, Watson sentiment analyzer, etc.) to search the one or more retrieved documents to produce one or more tokens from the one or more retrieved documents at step 410. A token may comprise a group of one or more related characters, symbols, terms, punctuation, phrases, and/or colloquialisms stored or located in the retrieved document. Framework 16 may further identify the presence of tokens based on one or more NLP dictionaries 27 of framework 16 and/or dictionary store 24 to generate one or more annotations associated with each identified token at step 415. An annotation may include information pertaining to output types, POS, values, processing rules and/or other features that may be associated with a token. An output type associated with a token may be utilized by rules processing module 22 to determine how to process one or more associated tokens. Framework 16 may search one or more NLP dictionaries 27 for the presence of a generated token to create an annotation for the generated token. The annotation and corresponding token may be stored in analytics store 26. The tokenization and dictionary matching phases (e.g., steps 410 and 415) may employ a state machine to perform the lexical analysis operations in a single pass.

Rules processing module 22 may parse the one or more retrieved documents to determine one or more patterns of the generated tokens and generate annotations based on rules associated with the one or more identified patterns at step 420. For example, rules processing module 22 may search for a token pattern of an "action" type followed by a "POS" type in the same sentence, and generate an annotation applying a corresponding rule to indicate that the action (e.g., walk, limp, etc.) pertains to needs assistance. According to an embodiment of the present invention, a rule may specify a configurable dictionary to search for the action, as described above.

The resulting one or more documents, which may include one or more annotations indicating whether one or more persons associated with the one or more documents need assistance with one or more activities, may be displayed to a user in real-time, i.e., as the user is consuming the retrieved document, at step 430, and process 400 ends.

Figure 5:
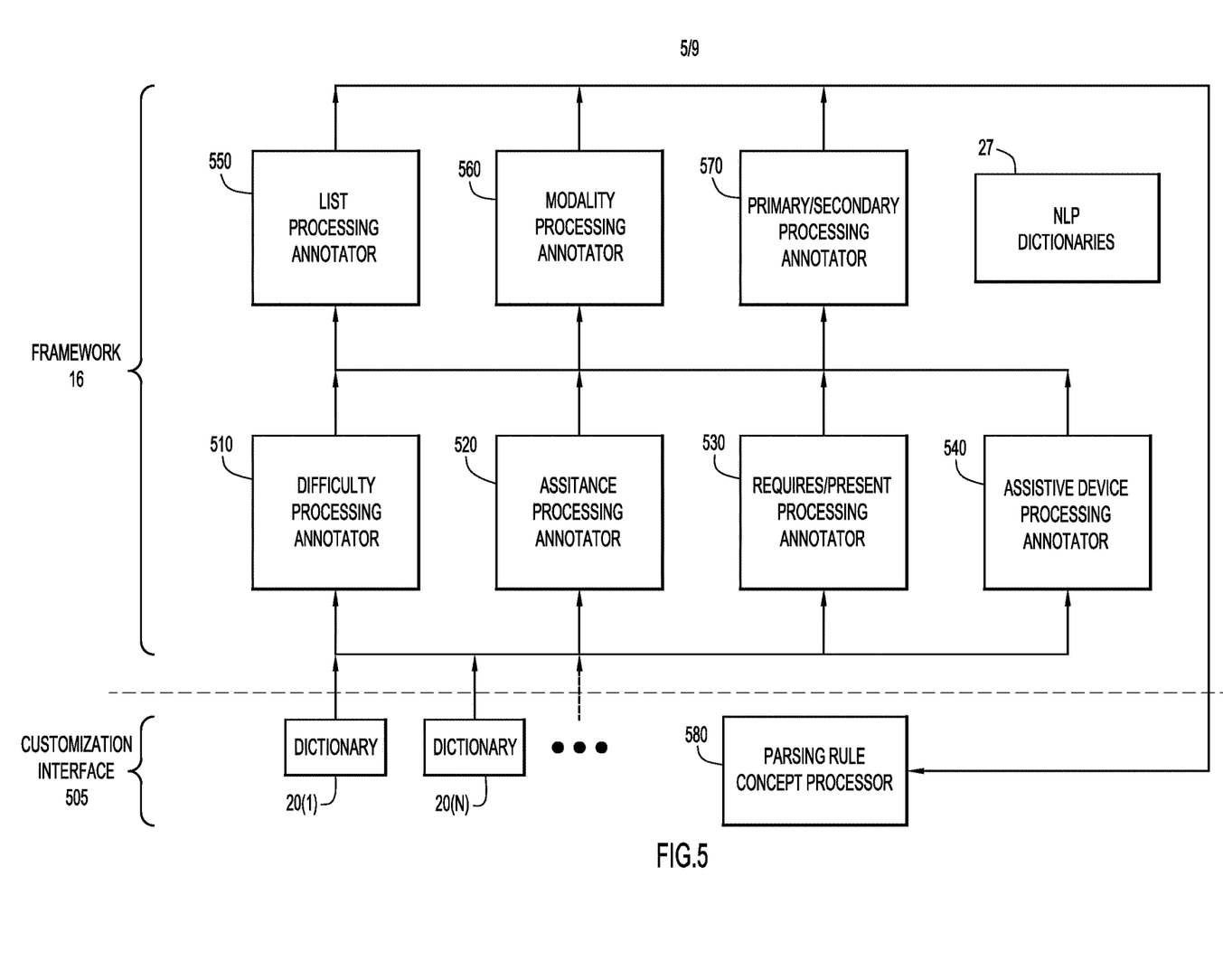
FIG. 5 is a diagrammatic illustration of an example framework employing configurable dictionaries for assistance needs detection according to an embodiment of the present invention.
Figure 6A:
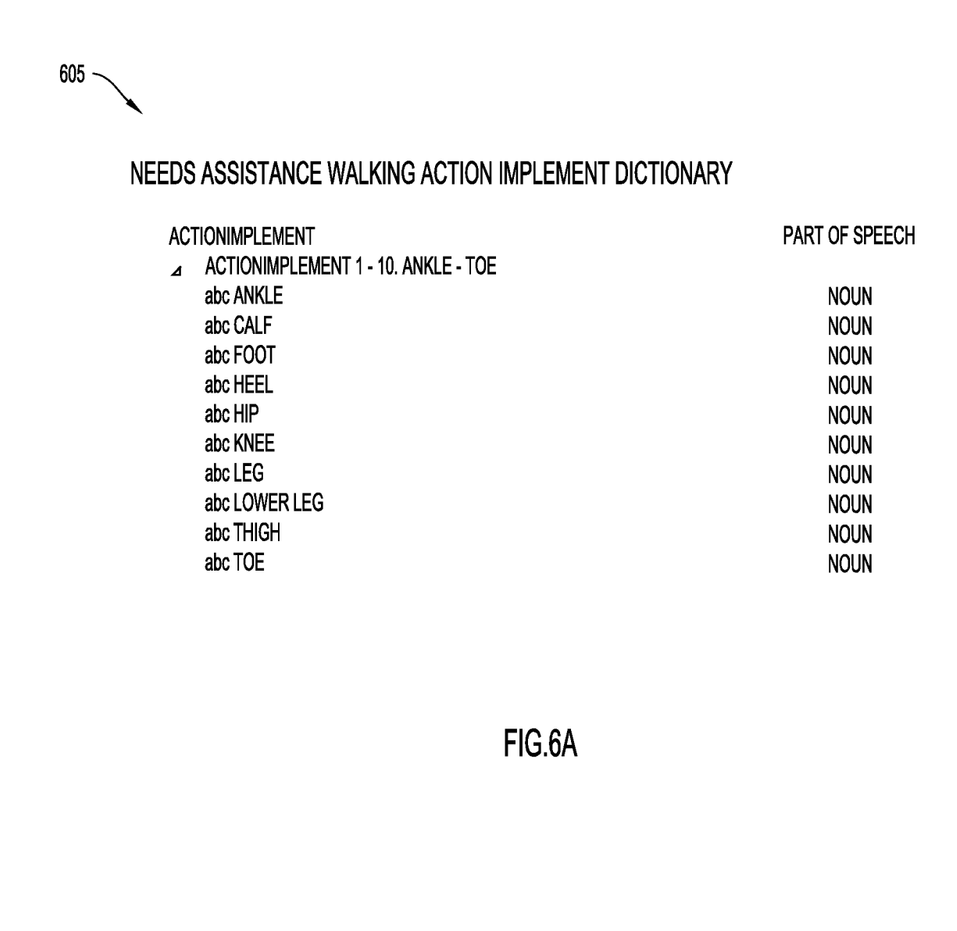
FIGS. 6A-6D are diagrammatic illustrations of example configurable dictionaries for the configurable framework according to an embodiment of the present invention.
Figure 6B:
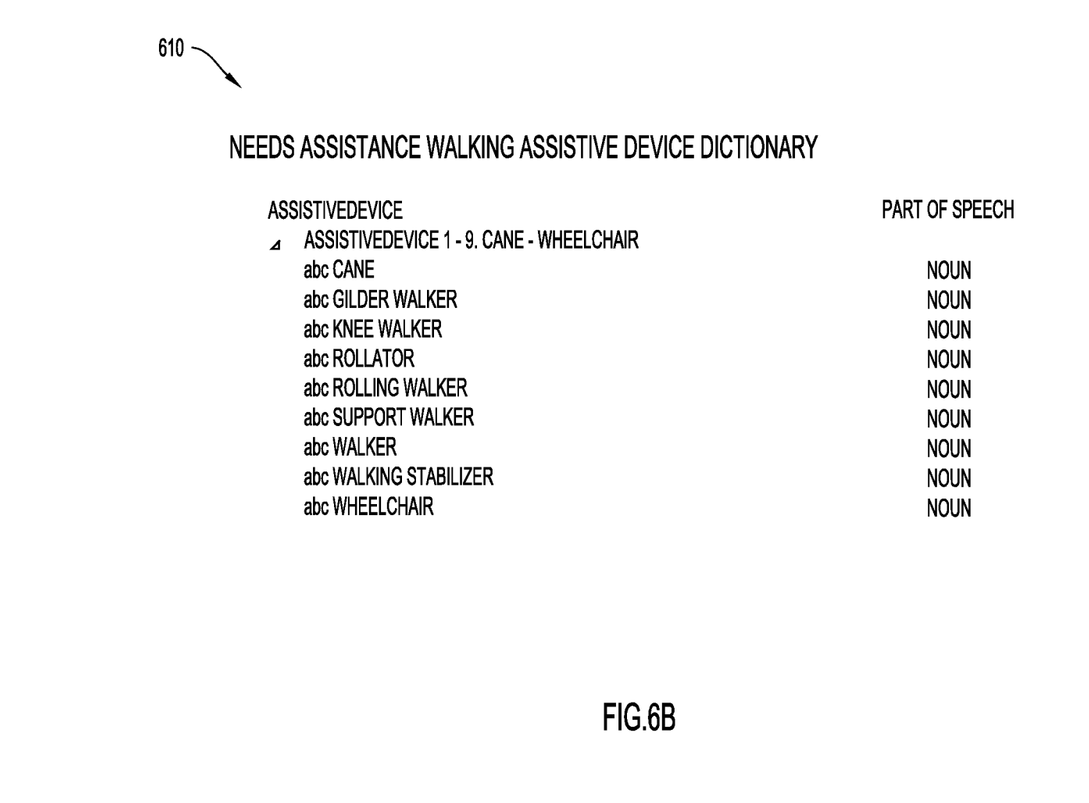
Figure 6C:
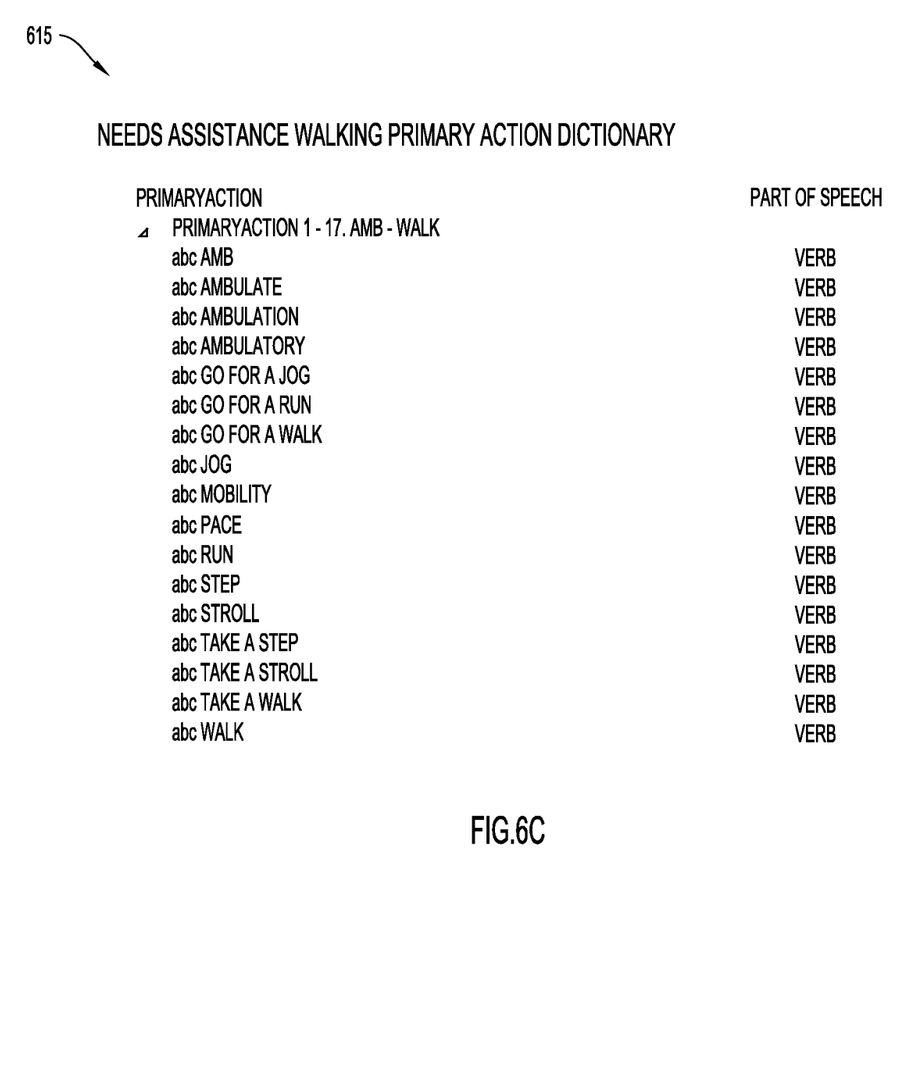
Figure 6D:
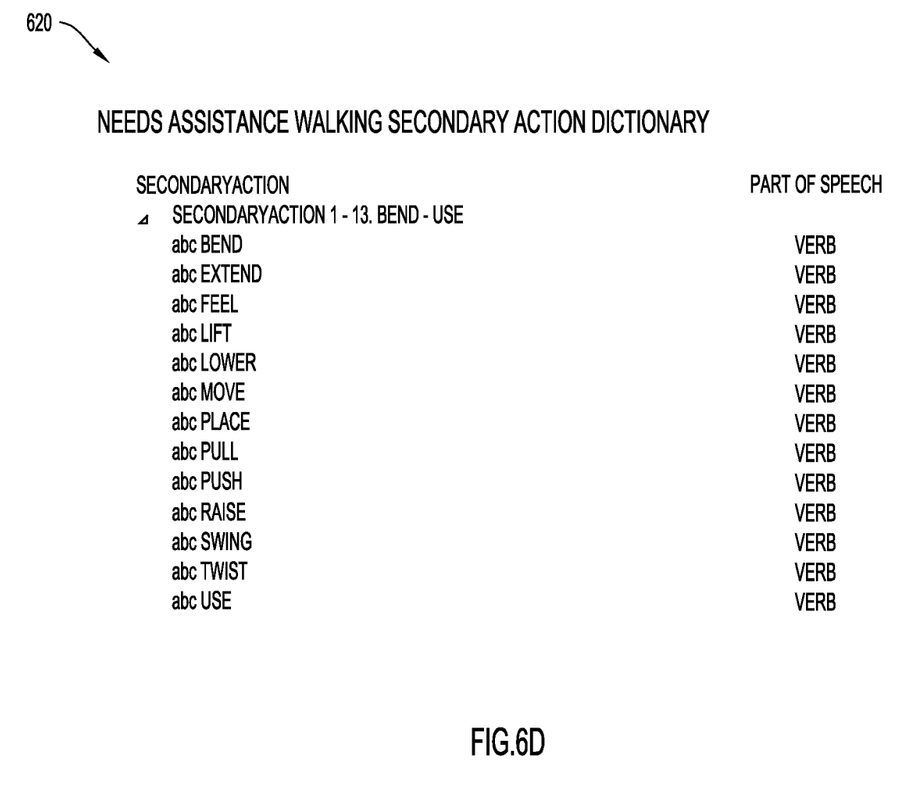

An environment 500 for determining needs assistance according to an embodiment of the present invention is illustrated in FIG. 5.

As shown in FIG. 5, environment 500 may comprise framework 16, which may include difficulty processing annotator 510, assistance processing annotator 520, requires/present processing annotator 530, assistive device processing annotator 540, list processing annotator 550, modality processing annotator 560, primary/secondary processing annotator 570, and a customization interface 505. The customization interface may include one or more configurable dictionaries 20(1)-20(N) and parsing rule concept processor 580. Difficulty processing annotator 510, assistance processing annotator 520, requires/present processing annotator 530, assistive device processing annotator 540, list processing annotator 550, modality processing annotator 560 and primary/secondary processing annotator 570 may annotate specific text occurring within a document (e.g., text, phrases, colloquialisms, and/or symbols) to indicate features in the text associated with a person needing assistance to perform one or more tasks related to a specific concept area.

One or more dictionaries 20 are configurable by a user associated with client systems 14 and may each contain a plurality of terms, phrases and/or symbols associated with a concept area in which one or more persons may need assistance to perform one or more tasks related to the concept area. According to an embodiment of the present invention, one or more dictionaries 20 may comprise a primary action dictionary, a secondary action dictionary, an action implement dictionary, and an assistive device dictionary. Primary action dictionary may contain terms associated with primary functions related to one or more activities. For example, if a document is related to a primary action of bathing, the primary actions dictionary may store terms, phrases and/or symbols related to one or more bathing activities (e.g., bathing, showering, washing, etc.) Similarly, if a document is related to a primary action of eating, primary action dictionary may store terms, phrases and/or symbols related to one or more eating activities (e.g., eating, chewing, etc.)

Secondary action dictionary may contain terms, phrases and/or symbols associated with actions that require additional confirmation whether they are related to the concept area being analyzed. To determine whether a secondary action is related to a concept area being analyzed, framework 16 may search action implement dictionary for terms or phrases, i.e., implements, that are targets for a given secondary action, that, when associated with the secondary action, indicate a concept area associated with the secondary action. For example, the term "holding" when associated with the work "fork," (e.g., the phrase "difficulty holding a fork") indicates eating assistance. Although "holding" may be a secondary action with respect to eating assistance, "holding" may not, in itself, be related to one or more eating activities. For example, the phrase "difficulty holding the door" is not related to eating assistance.

Similarly, assistive device dictionary may contain terms, phrases and/or symbols that reference one or more devices that may be used by one or more individuals to perform a specific action. For example, if a concept area being analyzed is walking, assistive device dictionary may contain a plurality of terms related to devices used to help a person to perform one or more walking activities (e.g., walker, cane, etc.).

In view of one or more configuration dictionaries 20, framework 16 may use lexical analytic and/or parsing rules (e.g., including references to one or more specific dictionaries 20 for terms) to detect language patterns within one or more received documents that indicate whether a person associated with the one or more received documents needs assistance performing one or more activities associated with a pre-configured concept area. According to an embodiment of the present invention, when determining whether a person needs assistance performing one or more activities, framework 16 gives priority to specific text (e.g., text, phrases, colloquialisms, and/or symbols), and/or synonyms or variations associated with the specific text, that directly indicates whether the person requires assistance to perform the one or more activities.

According to a further embodiment, an annotation created by framework 16 may contain a modality feature such that the annotation may be modified to indicate whether a person is "independent," "semi dependent," or "fully dependent." For example, if specific text within a document does not directly indicate whether a person associated with the document requires assistance, framework 16 may search the document for specific text and/or phrases indicating whether the person has difficulty or problems performing one or more specific tasks, and if so, difficulty processing annotator 510 may annotate the specific text and/or phrases to indicate a "semi dependent" state and/or modality associated with the person. The modality may be based on application of the rules to the document text.

As shown in FIG. 5, difficulty processing annotator 510, assistance processing annotator 520, requires/present processing annotator 530, and assistive device processing annotator 540 may search one or more configurable dictionaries 20 for terms and/or phrases associated with a given concept area and/or one or more tasks related to the concept area to generate a plurality of customizable annotations for specific text occurring within a document. For example, in view of one or more configurable dictionaries 20, framework 16 may search a document for language patterns and/or text (as specified in one or more rules referencing the configurable dictionaries as disclosed above) indicating that a person associated with the document requires assistance to perform one or more tasks related to a concept area to which the one or more dictionaries were preconfigured (e.g., walking, eating, bathing, etc.).

If framework 16 determines, based on the satisfaction of a rule, that a person associated with a document needs assistance, assistance processing annotator 520 may annotate specific text within the document to indicate that the person requires assistance to perform the one or more tasks related to the given concept area.

Similarly, framework 16 may search a document for language patterns and/or text (as specified in one or more rules) indicating that a person associated with the document requires and/or uses an assistive device to perform one or more tasks. If framework 16 determines, based on the satisfaction of a rule, that a document indicates that a person associated with the document requires and/or uses an assistive device, assistive device processing annotator 540 may annotate specific text within the document to include a requires assistance annotation comprising a corresponding modality feature to indicate that the person requires and/or uses the assistive device.

As further shown in FIG. 5, the annotated output of difficulty processing annotator 510, assistance processing annotator 520, requires/present processing annotator 530, and/or assistive device processing annotator 540 may be forwarded to the input of list processing annotator 550, modality processing annotator 560 and/or primary/secondary processing annotator 570. Accordingly, list processing annotator 550, modality processing annotator 560 and/or primary/secondary processing annotator 570 may further annotate one or more annotations of specific text received from processing annotator 510, assistance processing annotator 520, requires/present processing annotator 530, and/or assistive device processing annotator 540 to generate annotations that may indicate whether a needs assistance condition has been identified. According to an embodiment of the present invention, each of the annotators in framework 16 may perform one or more of the steps 410-430 of FIG. 4 to generate the annotations.

Specifically, primary/secondary processing annotator 570 may further annotate specific text to indicate whether an activity with which a person needs assistance is a primary activity or a secondary activity needing further confirmation that the activity is related to a concept area being analyzed. For example, primary/secondary processing annotator 570 may receive specific text annotated by difficulty processing annotator 510 indicating that a person associated with a received document has difficulty performing an activity, e.g., bathing, and, based on the annotated specific text, may further annotate the specific text to indicate that the annotated activity is a primary activity based on one or more rules. If an annotated activity is a secondary activity, e.g., holding, primary/secondary processing annotator 570 may add a secondary action annotation based on one or more rules indicating that further confirmation is necessary to determine whether the annotated activity is related to a concept area being analyzed, e.g., eating.

Similarly, modality processing annotator 560 may add an annotation based on one or more rules to indicate whether a person associated with a received document is "independent," "semi dependent," or "fully dependent." For example, modality processing annotator 560 may further annotate an annotation received from assistance processing annotator 520 to indicate that a person who needs assistance walking is "semi dependent." List processing annotator 550 may further annotate specific text in the form of a listing. According to an embodiment of the present invention, list processing annotator 550 may process one or more lists such that an annotation is applied to each item or term in the list. For example, when processing the phrase "unable to eat, walk, and run," list processing annotator 550 may apply a separate annotation to "eat", "walk", and "run."

The annotated output of list processing annotator 550, modality processing annotator 560 and/or primary/secondary processing annotator 570 may be forwarded to parsing rule concept processor 580, which may use a set of rules to display the annotated text to one or more users associated with client systems 14. According to an embodiment of the present invention, the rules may be reusable and based on configurable dictionaries 20 to display appropriate activity-related information.

One or more dictionaries 20 may be customized by one or more users associated with client systems 14 to include a plurality of terms and/or symbols related to a specific concept area and/or activity. Thus, framework 16 may utilize rules to generate assistance needed indicator terms and/or architecture from text within a received document and, based on the rules, output an annotated document to a common reusable layer that may be stored by parsing rules concept processor 580 for display to a user associated with client systems 14.

According to an embodiment of the present invention, one or more users associated with client systems 14 may further evaluate the rules, terms and/or architecture related to a concept area and generated by list processing annotator 550, modality processing annotator 560 and/or primary/secondary processing annotator 570 to determine whether needs assistance terms and/or symbols related to the concept area and/or activity should be added and/or removed from one or more dictionaries 20.

Example configurable dictionaries 20 that indicate a plurality of terms and/or phrases related to an activity, e.g., walking, and associated parts-of-speech (POS) according to an embodiment of the present invention are illustrated in FIGS. 6A-6D. It should be understood that the information for one or more configurable dictionaries 20 may be combined and stored in a single dictionary, or may be partitioned in any manner among any quantity of dictionaries based on any desired criteria. The POS associated with the terms and/or phrases enable rules processing module 22 to parse specific text occurring within a document (e.g., text, phrases, colloquialisms, and/or symbols) to identify needs assistance terms and/or phrases indicated in the specific text. For example, rule processing module 22 may parse specific text within a document to determine whether an individual needs assistance performing an activity, whether the activity is a primary or secondary activity, whether the individual needs and/or requires an assistive device or implement to perform the activity, whether the activity is a primary or secondary activity, and/or one or more areas of the individual that need assistance performing the activity.

An example implement dictionary 605 (FIG. 6A) may include one or more implements associated with an individual (e.g., legs, feet, knee, etc.) where assistance may be needed and/or required to perform a specific activity, e.g., walking, and a corresponding POS for each of the implements, e.g., noun. Needs assistance dictionary 605 may be represented as a table, where each row corresponds to a term (or implement) and the columns represent the POS associated with each term or phrase. By way of example, dictionary 605 may include the implements "ankle", "calf", "foot", "heel", "hip", "knee", "leg", "lower leg", "thigh" and "toe", each having a corresponding POS of a noun.

Example assistive device dictionary 610 (FIG. 6B) may include several assistive devices needed and/or required by an individual to perform a specific activity, e.g., walking, and a corresponding POS for each of the assistive devices, e.g., noun. This dictionary may be represented as a table as discussed above, where each row corresponds to an assistive device and the columns represent a POS for each device. By way of example, dictionary 610 may include the assistive devices "cane", "gilder walker", "knee walker", "rollator", "rolling walker", "support walker", "walker", "walking stabilizer", and "wheelchair", each having a corresponding POS of a noun.

Example primary action dictionary 615 (FIG. 6C) may include several primary actions that may indicate a specific activity, e.g., walking, and a corresponding POS for each of the primary actions, e.g., verb. This dictionary may be represented as a table as discussed above, where each row corresponds to a primary action and the columns represent a POS for each primary action. By way of example, dictionary 615 may include the primary actions "amb", "ambulate", "ambulation", "ambulatory", "go for a jog", "go for a run", "go for a walk", "jog", "mobility", "pace", "run", "step", "stroll", "take a step", "take a stroll", "take a walk", and "walk", each having a corresponding POS of a verb.

Example secondary action dictionary 620 (FIG. 6D) may include several secondary actions that may require further processing to confirm that the secondary action is related to a specific activity, e.g., walking. Secondary action dictionary 620 may further include a corresponding POS for each of the secondary actions, e.g., verb. This dictionary may be represented as a table as discussed above, where each row corresponds to a secondary action and the columns represent a POS for each secondary action. By way of example, dictionary 620 may include the primary actions "bend", "extend", "feel", "lift", "lower", "move", "place", "pull", "push", "raise", "swing", "twist", and "stroll", each having a corresponding POS of a verb.

Accordingly, because the rules reference one or more configurable dictionaries 20 and are re-usable, framework 16 may be configured (and generate annotators) for various activities by altering and/or modifying the terms in the one or more configurable dictionaries 20.

Advantages of the present invention embodiments include a framework that is easily configurable or customizable for any action and/or concept area, enabling developers to reuse the underlying source code for the framework to readily develop a plurality of needs assistance annotators, decreasing the time and expense associated with their development. Users of the configurable framework described herein may use object code for a framework rules processing portion and one or more configurable dictionaries as customization/configuration points for the framework to develop and/or fine tune the framework to identify, in real-time, needs assistance terms or phrases occurring within one or more documents associated with an individual and related to a specific concept area and/or activity. Accordingly, the disclosed system enables developers to quickly prototype and cost-effectively create a plurality of needs assistance annotators by modifying one or more configurable dictionaries.

Furthermore, if the framework determines that one more documents associated with a patient and/or client indicates a needs assistance condition, the framework may generate an alarm signal notifying a service care professional, in real-time, that a patient and/or client may need their assistance to perform one or more activities, or conduct an electronic transaction to purchase one or more assistive devices. For example, the disclosed framework may be readily configured to help a physician detect, in real-time, that a patient needs assistance to eat or to walk. Similarly, the framework may be modified to notify a financial advisor that a client requires help completing their taxes.

The disclosed system may further be used by a service care professional to identify, in real-time, an assistance need condition of a patient while the service care professional enters information associated with the patient into an electronic medical record (e.g., via text entry, voice/speech recognition, etc.). The system may further comprise a patient monitor that may detect a needs assistance condition associated with a patient (e.g., by monitoring vital signs, listening and processing user voice or speech, measuring ambient conditions, etc.) and, in response, forward an alarm signal to, or establish communication with, a service care professional and/or a first responder to provide the patient's location and/or type of assistance required (e.g., breathing, walking, etc.).

It will be appreciated that the embodiments described above and illustrated in the drawings represent only a few of the many ways of implementing embodiments for providing a configurable analytics framework for assistance needs detection.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.).

The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, rules processing module, etc.). These systems may include any types of monitors and input devices (e.g., keyboard, mouse, voice recognition, etc.) to enter and/or view information.

It is to be understood that the software (e.g., framework, rules processing module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., framework, rules processing module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., documents, terms or phrases, annotations, dictionaries, etc.). The database system may be implemented by any number of any conventional or other databases, data stores or storage structures (e.g., files, databases, data structures, data or other repositories, etc.) to store information (e.g. documents, terms or phrases, annotations, dictionaries, etc.). The database system may be included within or coupled to the server and/or client systems. The database systems and/or storage structures may be remote from or local to the computer or other processing systems, and may store any desired data (e.g., documents, terms or phrases, annotations, dictionaries, etc.).

The present invention embodiments may employ any number of any type of user interface (e.g., Graphical User Interface (GUI), command-line, prompt, etc.) for obtaining or providing information (e.g., documents, analytics, annotations, user or other preferences, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion. A report may include any information arranged in any fashion, and may be configurable based on rules or other criteria to provide desired information to a user (e.g., documents, analytics, annotations, user or other preferences, etc.).

The present invention embodiments are not limited to the specific tasks or algorithms described above, but may be utilized for any types of documents (e.g., web pages, word processing or other application (e.g., spreadsheets, presentations, etc.) documents, documents with structured and/or unstructured content, etc.) to detect any type of textual or other types of terms or phrases related to a topic, concept area and/or a specific activity. The terms and phrases may have any quantity of annotations for needs assistance. The annotations may include any identifiers, and contain any desired information and/or features (e.g., dictionary content, dictionary identifiers, operations, computation results, equivalent terms (e.g., slang, different words/phrases in the same or different native languages, etc.) to enable a user to identify a needs assistance condition. Further, the annotations may be provided for any quantity of terms or grouping of terms (e.g., one or more terms, phrases, clauses, sentences, paragraphs, pages, etc.). For example, phrase rules may be used to identify needs assistance and provide annotations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:
1. A method of processing a document including unstructured text comprising:
    configuring, via a processor, a plurality of dictionaries with user-supplied terms associated with a desired category, wherein the desired category includes an entity requiring assistance to perform a physical activity;

applying, via the processor, a set of rules to generate patterns for comparison with the unstructured text of the document to determine a presence of the desired category, wherein the set of rules is re-usable across dictionaries configured for different categories and pertains to arrangements of dictionary terms within sentences, wherein at least one rule references two or more of the plurality of dictionaries for the dictionary terms to generate the patterns, wherein a first dictionary term from the two or more dictionaries is associated with a plurality of physical activities and requires confirmation to be associated with the physical activity of the desired category, and wherein one or more additional dictionary terms from the two or more dictionaries provide the confirmation and associate the first dictionary term with the physical activity of the desired category;

detecting, via the processor, the patterns in the unstructured text of the document indicating the presence of the desired category;

generating, via the processor, annotations associated with the desired category for the document based on the detected patterns via a series of annotators that are re-usable across dictionaries configured for different categories; and changing, via the processor, the desired category to the entity requiring assistance to perform a different physical activity by providing the plurality of dictionaries with new dictionaries including user-supplied terms associated with the different physical activity, wherein the set of rules generates new patterns for the different physical activity based on the new dictionaries.

2. The method of claim 1, wherein the plurality of dictionaries includes:
a first dictionary comprising terms associated with functions related to the physical activity;
a second dictionary comprising terms associated with actions requiring implements;
a third dictionary comprising terms associated with the implements for the actions; and
a fourth dictionary comprising terms associated with devices used to assist the entity in performing the physical activity.

3. The method of claim 1, wherein generating the annotations further comprises:
applying dependence rules to the unstructured text and determining a dependence of the entity with respect to performing the physical activity; and
modifying a generated annotation to indicate the determined dependence of the entity, wherein the modified annotation indicates that the entity is one of independent, semi-dependent, and fully dependent relative to performing the physical activity.

4. The method of claim 1, wherein the entity requiring assistance is a medical patient.

5. The method of claim 4, wherein the physical activity is selected from a group consisting of standing, walking, eating, dressing, bathing, using a toilet, speaking, and administering a health substance.

6. A system for processing a document including unstructured text comprising:
a computer system including at least one processor configured to:
configure a plurality of dictionaries with user-supplied terms associated with a desired category, wherein the desired category includes an entity requiring assistance to perform a physical activity;
apply a set of rules to generate patterns for comparison with the unstructured text of the document to determine a presence of the desired category, wherein the set of rules is re-usable across dictionaries configured for different categories and pertains to arrangements of dictionary terms within sentences, wherein at least one rule references two or more of the plurality of dictionaries for the dictionary terms to generate the patterns, wherein a first dictionary term from the two or more dictionaries is associated with a plurality of physical activities and requires confirmation to be associated with the physical activity of the desired category, and wherein one or more additional dictionary terms from the two or more dictionaries provide the confirmation and associate the first dictionary term with the physical activity of the desired category;
detect the patterns in the unstructured text of the document indicating the presence of the desired category;
generate annotations associated with the desired category for the document based on the detected patterns via a series of annotators that are re-usable across dictionaries configured for different categories; and
change the desired category to the entity requiring assistance to perform a different physical activity by providing the plurality of dictionaries with new dictionaries including user-supplied terms associated with the different physical activity, wherein the set of rules generates new patterns for the different physical activity based on the new dictionaries.

7. The system of claim 6, wherein the plurality of dictionaries includes:
a first dictionary comprising terms associated with functions related to the physical activity;
a second dictionary comprising terms associated with actions requiring implements;
a third dictionary comprising terms associated with the implements for the actions; and
a fourth dictionary comprising terms associated with devices used to assist the entity in performing the physical activity.

8. The system of claim 6, wherein generating the annotations further comprises:
applying dependence rules to the unstructured text and determining a dependence of the entity with respect to performing the physical activity; and
modifying a generated annotation to indicate the determined dependence of the entity, wherein the modified annotation indicates that the entity is one of independent, semi-dependent, and fully dependent relative to performing the physical activity.

9. The system of claim 6, wherein the entity requiring assistance is a medical patient.

10. The system of claim 9, wherein the physical activity is selected from group consisting of standing, walking, eating, dressing, bathing, using a toilet, speaking, and administering a health substance.

11. A computer program product for processing a document including unstructured text comprising:

a computer readable storage medium having program instructions embodied therewith, the program instructions executable by a processor to cause the processor to:
  configure a plurality of dictionaries with user-supplied terms associated with a desired category, wherein the desired category includes an entity requiring assistance to perform a physical activity;
  apply a set of rules to generate patterns for comparison with the unstructured text of the document to determine a presence of the desired category, wherein the set of rules is re-usable across dictionaries configured for different categories and pertains to arrangements of dictionary terms within sentences, wherein at least one rule references two or more of the plurality of dictionaries for the dictionary terms to generate the patterns, wherein a first dictionary term from the two or more dictionaries is associated with a plurality of physical activities and requires confirmation to be associated with the physical activity of the desired category, and wherein one or more additional dictionary terms from the two or more dictionaries provide the confirmation and associate the first dictionary term with the physical activity of the desired category;
  detect the patterns in the unstructured text of the document indicating the presence of the desired category;
  generate annotations associated with the desired category for the document based on the detected patterns via a series of annotators that are re-usable across dictionaries configured for different categories; and
  change the desired category to the entity requiring assistance to perform a different physical activity by providing the plurality of dictionaries with new dictionaries including user-supplied terms associated with the different physical activity, wherein the set of rules generates new patterns for the different physical activity based on the new dictionaries.

12. The computer program product of claim 11, wherein the plurality of dictionaries includes:
  a first dictionary comprising terms associated with functions related to the physical activity;
  a second dictionary comprising terms associated with actions requiring implements;
  a third dictionary comprising terms associated with the implements for the actions; and
  a fourth dictionary comprising terms associated with devices used to assist the entity in performing the physical activity.

13. The computer program product of claim 11, wherein generating the annotations further comprises:
  applying dependence rules to the unstructured text and determining a dependence of the entity with respect to performing the physical activity; and
  modifying a generated annotation to indicate the determined dependence of the entity, wherein the modified annotation indicates that the entity is one of independent, semi-dependent, and fully dependent relative to performing the physical activity.

14. The computer program product of claim 11, wherein the entity requiring assistance is a medical patient.

15. The computer program product of claim 14, wherein the physical activity is selected from a group consisting of standing, walking, eating, dressing, bathing, using a toilet, speaking, and administering a health substance.

* * * * *